United States Patent [19]

Garvin et al.

[11] 4,307,035
[45] Dec. 22, 1981

[54] METHOD OF SYNTHESIZING RESIN PREPOLYMERS

[75] Inventors: Carl J. Garvin, Pensacola, Fla.; Teddy M. Keller, Alexandria, Va.

[73] Assignee: The United States of America as represented by the Secretary of the Navy, Washington, D.C.

[21] Appl. No.: 175,454

[22] Filed: Aug. 5, 1980

[51] Int. Cl.³ ............................................. C07C 121/78
[52] U.S. Cl. ................................................. 260/465 E
[58] Field of Search ..................................... 260/465 E

[56] References Cited

U.S. PATENT DOCUMENTS

| 4,057,569 | 11/1977 | Griffith et al. | 260/465 E |
| 4,116,945 | 9/1978 | Griffith et al. | 528/362 |
| 4,136,107 | 1/1979 | Griffith et al. | 260/465 E |

Primary Examiner—Dolph H. Torrence

Attorney, Agent, or Firm—R. S. Sciascia; A. L. Branning; T. E. McDonnell

[57] ABSTRACT

An improved method of synthesizing bisorthodinitriles having the formula:

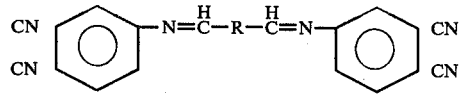

where R is an aliphatic or aromatic radical, which involves dissolving the reactants in a dipolar aprotic solvent such as dimethylformamide, and heating the mixture to reflux until the completion of the reaction. The usage of such solvents permits the reaction to be completed at least ten times as fast as the prior-art method, while the volume of solvent used is also reduced by a factor of ten.

5 Claims, No Drawings

METHOD OF SYNTHESIZING RESIN PREPOLYMERS

BACKGROUND OF THE INVENTION

This invention pertains to a method of synthesizing organic prepolymers, and, more particularly, to an improved method of synthesizing bisorthodinitriles using a dipolar aromatic solvent as the reaction medium.

Current methods of synthesizing bisorthodinitriles and the cyanocondensation resins prepared therefrom have been detailed, for example, in U.S. Pat. Nos. 3,993,631; 4,056,560; 4,057,569; 4,067,860 and 4,116,945. The references: 4,057,569 and 4,116,945 disclose that disorthodinitriles of the generic formula:

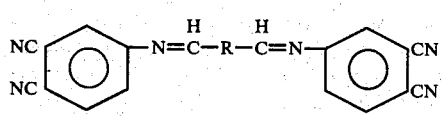

wherein R is an aliphatic or aromatic radical can be prepared by reacting 4-aminophthalonitrile with the appropriate di-aldehyde in a refluxing solvent, such as benzene, toluene, chlorobenzene, anisole, or the like. The synthesis involving terephthaldehyde proceeds as follows:

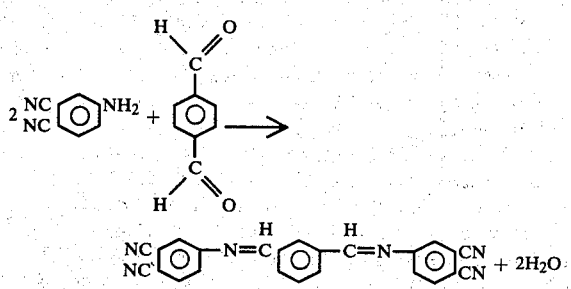

This reaction, however, is flawed by the fact that a great amount of solvent is required in order to produce a small amount of the bisorthodinitrile, since large amounts of these solvents are required to dissolve the reactants. This necessitates large size reaction vessels, which leads to a very cumbersome production method. An even more serious flaw is that the reaction is a very slow one, often taking several days to produce product yields in the area of 35%.

SUMMARY OF THE INVENTION

It is therefore, an object of this invention to provide an improved method of preparing a class of bisorthodinitrile compounds.

It is another object of this invention to provide a method of preparing bisorthodinitriles which preceeds much faster, is much less cumbersome, and furnishes a greater product yield than currently used techniques.

It is a still further object of this invention to provide a method which may enable further synthetic research using reactants whose rate of reaction would otherwise prove to be too slow for practical applications.

These and other objects are achieved by an improved method of preparing bisorthodinitriles of the formula:

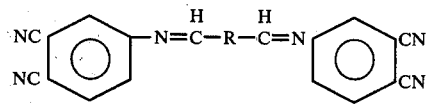

where R is an aliphatic or aromatic radical, comprising mixing a slight stoichiometric excess of 4-aminophthalonitrile with a suitable di-aldehyde in a dipolar aprotic solvent such as dimethylformamide (DMF) or the like. The reactants are heated and refluxed for a period of 1-3 hours, whereupon the solution is cooled while the product precipitates, and is later separated from the mixture.

DETAILED DESCRIPTION OF THE INVENTION

The following process is typical of the techniques currently used in synthesizing bisorthodinitriles:

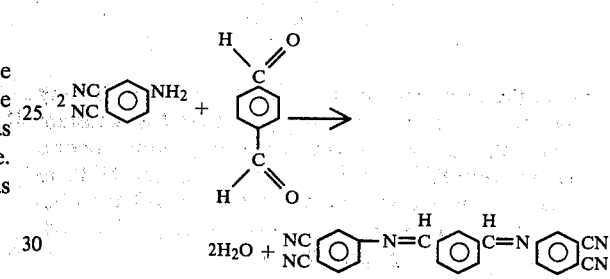

A slight excess of 4-aminophthalonitrile is used to ensure the reaction of both aldehyde groups, generally about 5 to 15 percent in excess of the stoichiometric amount, which is two moles of 4-aminophthalonitrile for each mole of the aldehyde terminated reactant. Using this technique, 12.1 grams (0.0903) of terephthaldehyde recrystallized from toluene were mixed with 28.3 grams (0.1980 moles) of 4-aminophthalonitrile, and 1.420 liters of toluene solvent were charged into a three liter round bottomed flask fitted with a thermometer, a Dean-Stark trap under a water-cooled condenser, heating mantle, and stirrer. The reaction mixture is heated to reflux and allowed to proceed for about three days. This technique is reported to produce product yields in excess of 70% of the theoretical amount.

Although applicants do not wish to be bound by theory, it is believed that the electron rich amino nitrogens attack the electrons deficient carbon aldehyde, and in so doing, form a C=N moiety, together with the formation of a water molecule which water molecule is then removed from the system, e.g., by use of an azeotroping agent.

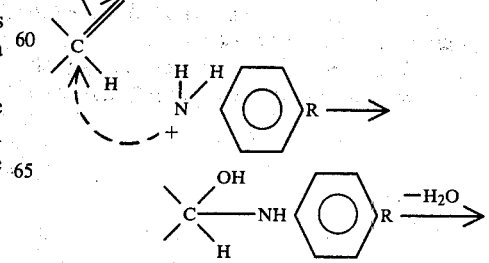

-continued

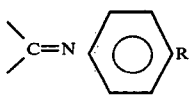

If such is the mechanism of the reaction, the usage of a dipolar aprotic solvent, such as dimethylformamide (DMF)

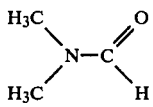

dimethyl sulfoxide (DMSO),

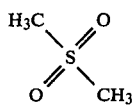

or, in the broadest embodiment of the invention, any dipolar aprotic solvent having a dielectric constant greater than about 16 such as hexamethylphosphoric triamide (HMPT), 1-methyl-2-pydolidone, N, N-dimethylacetamide and the like will be suitable. This is believed to be due to the fact that the polarity of the solvent in solution, e.g., for DMF:

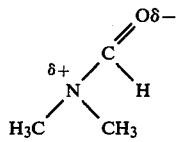

enables the reactants to go into solution much faster, and further aids the reaction rate, whereas the weak organic polar solvents which has been previously used do not actively aid this reaction mechanism.

The preparation of 4-aminophthalonitrile is not a part of this invention, but can be done by the method stated in U.S. Pat. No. 3,993,631, for example. Similiarly, the aldehydes and solvents used in the process can be easily obtained from a great number of well known commercial suppliers.

EXAMPLE 1

Preparation of Bis(3,4-dicyanoaniline) N, N'-p-xylylenediidene 10.8 grams of 4-aminophthalonitrile, and 4.8 grams of terephthaldehyde were dissolved in 50 ml of DMF in a 300 ml 3-neck reaction flask, and were heated on an oil bath for two hours. Benzene was added to the solution as an azeotroping agent for the removal of H₂O. After refluxing for two hours, the flask was allowed to cool to room temperature causing the product to precipitate. The product was filter out and recrystallized in acetonitrile (at this concentration of DMF, ppt. occurs at a reaction T of 100° C.). The total yield of product is 8.30 grams, or 59.7% yield.

EXAMPLE 11

The same proportions of reactants used in Example I were added to a 100 ml 3 neck reaction flask, together with 10 ml of DMF. The flask was fitted with a thermometer, a Dean Stark trap (filled with benzene), a condensor and stopper. The reactants were heated to hasten being dissolved in DMF. The reactants were next heated and refluxed for a period of one hour, until 1.3 ml of H₂O had been collected. The product was then precipitated out of the reaction mixture, filtered, and washed several times with CHCl₃, then recrystallized in acetonitrile. 9.8 grams of product were recovered, a 70.5% yield of reaction product, verified by I.R. techniques.

As indicated above, a suitable amount of an azeotroping agent such as benzene can be included in the solvent mixture in order to remove the H₂O reaction product from the mixture. Such agents and techniques are well known in the art.

The method of the above invention now permits bisorthodinitriles to be synthesized in a matter of hours, instead of the days required by the use of weak polar organic solvents. Since a tremendous amount of solvent was formerly required to dissolve even the smallest amount of reactants, this leads to an extremely bulky reaction method which greatly hampers research efforts in this area by making synthesis of bisorthodinitriles a lengthly, time-consuming and expensive task. Since many of these solvent bases usable in this invention are hydrolytically unstable, the art has avoided their use in such reactions; however, their properties will now be more fully investigated.

Obviously many modifications and variations of the present invention are possible in light of the above teachings. It is therefore to be understood that within the scope of the appended claims the invention may be practiced otherwise then as specifically described.

What is claimed and desired to be secured by Letters Patent of the United States is:

1. In a method for synthesizing phthalonitrile resins prepolymers which comprises admixing 4-aminophthalonitrile with a di-aldehyde in a solvent to form a fluid mixture, heating said mixture to reflux, whereby 4-aminophthalo-nitrile reacts with said di-aldehyde to form said phthalonitrile resin prepolymer, cooling said mixture to precipitate said phthalonitrile resin prepolymer, and separating said phthalonitrile resin prepolymers, the improvement which comprises selecting a dipolar aprotic solvent as said solvent.

2. The method of claim 1 wherein said solvent is selected from the class consisting of dimethylformamide and dimethyl sulfoxide.

3. The method of claim 1 wherein said solvent is dimethylformamide.

4. The method of claims 1, 2, or 3, wherein an isomer of phthaldehyde is selected as said di-aldehyde.

5. The method of claims 1, 2, or 3 wherein terephthaldehyde is selected as said di-aldehyde.

* * * * *